US012661174B2

(12) United States Patent
Küster

(10) Patent No.: US 12,661,174 B2
(45) Date of Patent: Jun. 23, 2026

(54) SURGICAL EQUIPMENT SOCKET, SURGICAL GENERATOR, SURGICAL SYSTEM AND METHOD FOR DETECTING THE USE OF A SURGICAL INSTRUMENT IN A SURGICAL SYSTEM

(71) Applicant: OLYMPUS WINTER & IBE GMBH, Hamburg (DE)

(72) Inventor: Oliver Küster, Potsdam (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 493 days.

(21) Appl. No.: 18/176,200

(22) Filed: Feb. 28, 2023

(65) Prior Publication Data

US 2023/0293223 A1 Sep. 21, 2023

Related U.S. Application Data

(60) Provisional application No. 63/321,841, filed on Mar. 21, 2022.

(51) Int. Cl.
*H01R 27/00* (2006.01)
*A61B 18/12* (2006.01)
(Continued)

(52) U.S. Cl.
CPC ....... *A61B 18/1206* (2013.01); *H01R 13/641* (2013.01); *H01R 27/00* (2013.01); *H01R 29/00* (2013.01); *A61B 17/320068* (2013.01); *A61B 2018/00178* (2013.01); *A61B 2090/0808* (2016.02); *H01R 2201/12* (2013.01)

(58) Field of Classification Search
CPC ...... H01R 27/00; H01R 13/641; H01R 29/00; H01R 2201/12
See application file for complete search history.

(56) References Cited

U.S. PATENT DOCUMENTS 5,302,141 A * 4/1994 O'Reilly ................ H01R 27/00
439/680
5,540,683 A 7/1996 Ichikawa et al.
(Continued)

FOREIGN PATENT DOCUMENTS

EP 0 947 167 A1 10/1999
EP 2 329 783 A1 6/2011
(Continued)

OTHER PUBLICATIONS

Jan. 23, 2024 Office Action Issued in Japanese Patent Application No. 2023-044516.
(Continued)

*Primary Examiner* — Oscar C Jimenez
(74) *Attorney, Agent, or Firm* — Oliff PLC

(57) ABSTRACT

A surgical equipment socket for a surgical generator for connecting surgical instruments, a surgical system and a method for detecting the use of a surgical instrument in a surgical system, wherein the surgical equipment socket includes a first indicator assembly having a first movable element, and a first detection element; wherein the first movable element is movable from a free position to a mated position, and wherein the first detection element is adapted to detect whether the first movable element is in the mated position.

16 Claims, 5 Drawing Sheets

Figure 1:
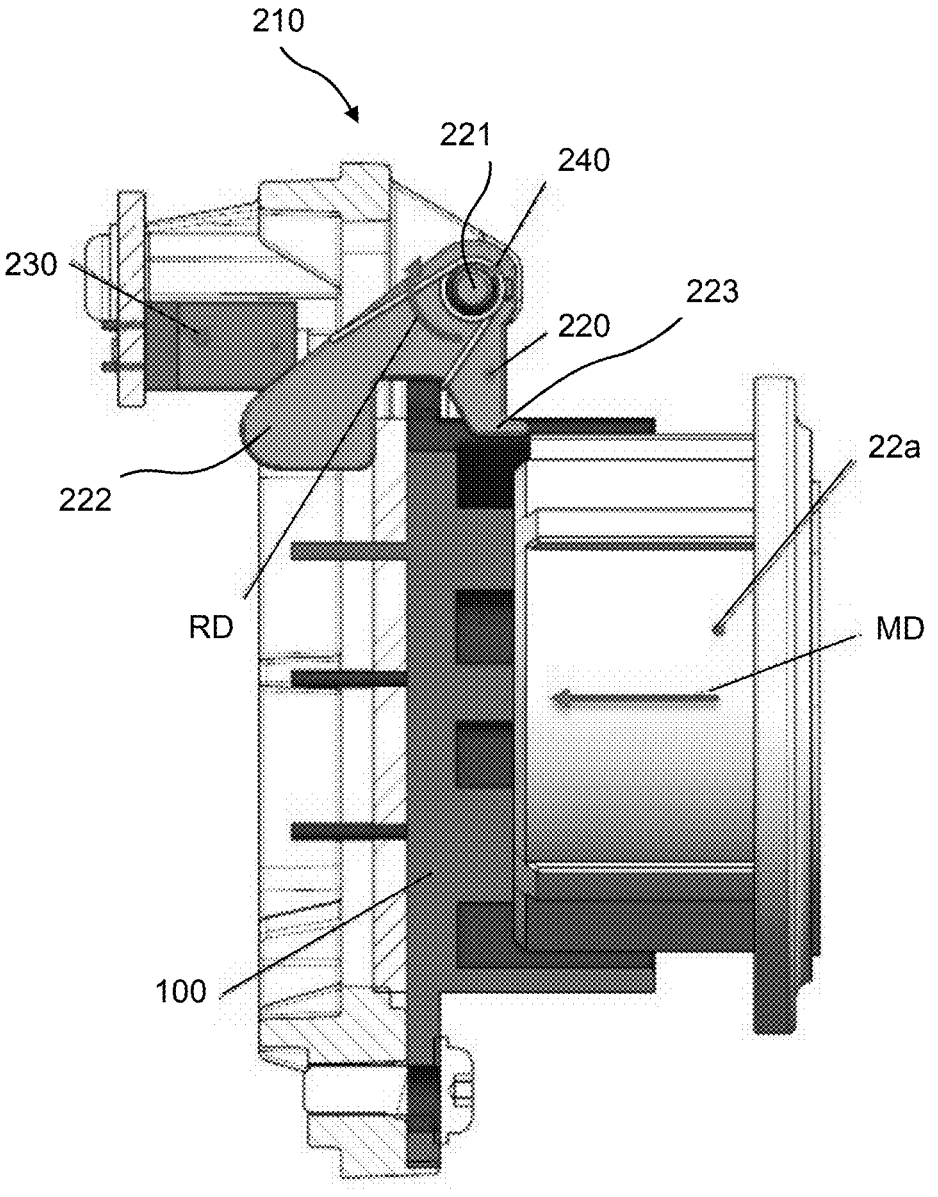

(51) Int. Cl.
    *A61B 90/00*         (2016.01)
    *H01R 13/641*      (2006.01)
    *H01R 29/00*       (2006.01)
    *A61B 17/32*       (2006.01)
    *A61B 18/00*       (2006.01)

(56)          References Cited

U.S. PATENT DOCUMENTS

| | | | |
|---|---|---|---|
| 6,141,212 A * | 10/2000 | Fletcher | H01R 27/00 |
| | | | 361/679.45 |
| 10,772,673 B2 * | 9/2020 | Allen, IV | A61B 18/1815 |
| 11,759,271 B2 * | 9/2023 | Laubenthal | A61B 34/30 |
| | | | 606/1 |
| 2004/0036273 A1 * | 2/2004 | McClary | H01R 13/641 |
| | | | 285/18 |
| 2009/0215322 A1 * | 8/2009 | Omori | A61B 1/00128 |
| | | | 439/692 |
| 2012/0202388 A1 * | 8/2012 | Selig | A61B 18/14 |
| | | | 439/656 |
| 2014/0128886 A1 | 5/2014 | Holop et al. | |
| 2016/0066915 A1 | 3/2016 | Baber et al. | |
| 2016/0344131 A1 * | 11/2016 | Kanamori | H01R 13/447 |

FOREIGN PATENT DOCUMENTS

| | | |
|---|---|---|
| JP | H03-58408 U | 6/1991 |
| JP | H06-292684 A | 10/1994 |
| JP | H11-318921 A | 11/1999 |
| JP | 2010251198 A | 11/2010 |
| JP | 2015-535193 A | 12/2015 |
| WO | 2018/053539 A1 | 3/2018 |

OTHER PUBLICATIONS

Aug. 8, 2023 Extended Search Report issued in European Patent Application No. 23162206.9.
Jan. 4, 2023 Office Action issued in German Patent Appliation No. 10 2022 106 732.7.
Mar. 10, 2026 Office Action issued in Chinese Patent Application No. 202310280393.5.

* cited by examiner

1000

SURGICAL EQUIPMENT SOCKET, SURGICAL GENERATOR, SURGICAL SYSTEM AND METHOD FOR DETECTING THE USE OF A SURGICAL INSTRUMENT IN A SURGICAL SYSTEM

The invention relates to a surgical equipment socket for a surgical generator for connecting surgical instruments, a surgical generator, a surgical system and a method for detecting the use of a surgical instrument in a surgical system. In particular, the invention relates to a surgical equipment socket for a high-frequency generator and/or an ultrasound generator, a high-frequency generator and/or an ultrasound generator. In particular, the surgical equipment socket is adapted for connecting surgical instruments to a surgical generator.

In surgery, in particular electro and or ultrasound surgery, safety of the applied equipment, of the patients and the medical staff is of high importance. At the same time, it is desired to carry out surgical procedures in an easy and error-free manner. In this context, creating correct and intended connections between surgical instruments and a surgical generator is desired. While surgical equipment sockets exist and offer various advantages, further improvements are desirable.

It is therefore the object of the present invention to provide a surgical equipment socket for a surgical generator, a surgical generator, a surgical system and a method for detecting the use of a surgical instrument in a surgical system, which are improved compared to existing sockets, generators, systems and methods. It is, in particular, an object of the present invention to provide a surgical equipment socket for a surgical generator, a surgical generator, a surgical system and a method for detecting the use of a surgical instrument in a surgical system, which provide for a compact and reliable solution.

According to a first aspect, it is provided a surgical equipment socket for a surgical generator, in particular a high-frequency generator and/or an ultrasound generator, for connecting surgical instruments, the surgical equipment socket comprising a first indicator assembly having a first movable element, and a first detection element; wherein the first movable element is movable from a free position to a mated position, and wherein the first detection element is adapted to detect whether the first movable element is in the mated position.

The first indicator assembly of the surgical equipment socket allows for detecting whether the first movable element of said first indicator assembly is in a mated position or in a free position.

In particular, the mated position of the first movable element corresponds to a position, where a plug of a surgical instrument is inserted into the surgical equipment socket, in particular a plug of a surgical instrument that is adapted to move the first movable element from its free into its mated position upon insertion of such a plug into the surgical equipment socket. The free position preferably corresponds to a position, where no such plug is inserted in the surgical equipment socket, i.e., a position, in which the surgical equipment socket is free from such a plug.

As will be described further below, a plug of different kind of surgical instrument, which is not adapted to move the first movable element from its free into its mated position may be inserted into the surgical equipment socket, while the first movable element remains in its free position.

This has the advantage, that it can be detected via the first indicator assembly whether or not a plug, which adapted to move the first movable element from its free into its mated position upon its insertion into the surgical equipment socket is actually inserted in the surgical equipment socket or not.

Further, there may be plugs which are not suitable for moving the first movable element from the free to the mated position. Therefore, if a plug is present in the surgical equipment socket but the first movable element is not in the mated position, such a plug can be distinguished from another kind of plug, which does move the first movable element into the mated position upon its insertion into the surgical equipment socket. Therefore, the surgical equipment socket allows for certain degree of distinction of different kind of plugs inserted into the socket.

In particular, the surgical equipment socket is adapted for connecting, preferably different, surgical instruments, such as hybrid instruments for high-frequency and ultrasound energy on the one hand and ultrasound devices on the other hand. Thus, for example, it can be distinguished with the surgical equipment socket described herein, whether a hybrid instrument for high-frequency and ultrasound energy or and ultrasound device is inserted into the surgical equipment socket.

In the following, initially the surgical equipment socket and its components, functions and advantageous embodiments will be described. Further, details, functions and advantageous embodiments of the surgical generator, surgical system and method for detecting the use of a surgical instrument in a surgical system will be described.

As to the advantages, preferred embodiments and details of the aspects of the surgical equipment socket, the surgical generator, surgical system and method for detecting the use of a surgical instrument in a surgical system and their respective preferred embodiments, reference is made to the advantages, preferred embodiments and details described herein. In particular, the advantages, preferred embodiments and details described herein apply, mutatis mutandis, to all aspects mentioned herein, respectively.

In a preferred embodiment, the surgical equipment socket comprises a second indicator assembly having a second movable element, and a second detection element; wherein the second movable element is movable from a free position to a mated position, and wherein the second detection element is adapted to detect whether the second movable element is in the mated position.

Preferably, the first and second indicator assemblies can be configured in a similar manner or identically. Therefore, unless stated otherwise, the details and advantages described with respect to the first indicator assembly likewise apply to the second indicator assembly and vice versa.

Providing for a second indicator assembly has the advantage that further detection options arise. For example, different surgical instruments having different plugs may, upon insertion into the surgical equipment socket, move the first detection element of the first movable element of the first indicator assembly into the mated position, move the second movable element of the second indicator assembly into the mated position or move both the first and second movable elements of the first and second indicator assemblies or none of them into the mated position.

Further, preferably, a third indicator assembly and/or possibly more indicator assemblies may be provided, which again can be configured in a similar or identical manner, like the first and/or second indicator assembly.

According to a further preferred embodiment, the first movable element is movable in a rotational movement direction from the free position to the mated position, and/or the first movable element is rotatably supported about a first pivot axis. According to a further preferred embodiment, the second movable element is movable in a rotational movement direction from the free position to the mated position, and/or the second movable element is rotatably supported about a second pivot axis.

A bearing of the first and/or second movable element about a first and/or second pivot axis and/or rotating the first and/or second movable element from the free position to the mated position, and preferably vice versa, in a rotational direction has several advantages. This structure is space-saving and/or facilitates mounting and/or production of the surgical equipment socket. Further, this structure and the rotational movement are associated with very little friction and/or very little wear.

Further, a rotational movement reduces the risk of jamming or tilting and/or increases reliability of the movement. In particular, this structure is less sensitive to dirt and/or deposits, and thus also increases the safety and reliability.

It can be further preferred that the first movable element is movable in a linear motion from the free position to the mated position, and/or that the second movable element is movable in a linear motion from the free position to the mated position.

According to a preferred embodiment, the first indicator assembly comprises a first return element, wherein the first return element is adapted to move the first movable element from the mated position to the free position. According to a further preferred embodiment, wherein the second indicator assembly comprises a second return element, wherein the second return element is adapted to move the second movable element from the mated position to the free position.

Further preferably, the first and/or second movable element is/are also movable from the mated position to the free position. Further preferably, this movement is effected by a first and/or second return element, which is adapted to move the first and/or second movable element from the mated position to the free position.

By providing for a first and/or second return element, it can be ensured that, preferably once the plug is removed from the surgical equipment socket, the first and/or second movable element is/are restored from the mated position back into the free position. Preferably, the first and/or second movable element is/are biased in the free position.

In particular, it can be preferred that the first movable element is movable in a, preferably partially open or closed, first guide sleeve from the free position to the mated position. Further, it can be it can be preferred that the first return element is arranged in the first guide sleeve and/or the first return element is arranged in extension of the linear movement direction of the first movable element. According to a preferred embodiment, the second movable element is movable in a, preferably partially open or closed, second guide sleeve from the free position to the mated position.

According to a further preferred embodiment, the second return element is arranged in the second guide sleeve and/or the second return element is arranged in extension of the linear movement direction of the second movable element.

Further preferably, a detection direction of the first detection element is orthogonal to the linear movement direction of the first movable element. It is further preferred that a detection direction of the second detection element is orthogonal to the linear movement direction of the second movable element.

In particular, it is preferred that the first detection element comprises a switch, for example an optical switch and/or a light barrier and/or a contact switch, and/or a sensor, for example a Hall sensor. It is further preferred that the second detection element comprises a switch, for example an optical switch and/or a light barrier and/or a contact switch, and/or a sensor, for example a Hall sensor. These embodiments are particularly preferred in order to provide a solution, which is reliable and/or cost-effective and/or easy to produce and/or easy to mount.

In a further preferred embodiment, the first indicator assembly and the second indicator assembly are spaced apart circumferentially.

Further preferably, in case that a third indicator assembly and/or more indicator assemblies are provided, preferably all indicator assemblies are spaced apart circumferentially, preferably in equidistant manner.

In a further preferred embodiment, the first movable element has a first detection portion and a first plug contact portion, and/or the second movable element has a second detection portion and a second plug contact portion.

Preferably, the first and/or second detection portion is/are arranged such that in the mated position, the first and/or second detection portion activates the first and/or second detection element, respectively, in order for the first and/or second detection element to detect that the respective first and/or second movable element is in the mated position. Further preferably, the first and/or second plug contact portion is arranged such that the first and/or second plug contact portion contacts a first and/or second plug, respectively, upon its insertion into the surgical equipment socket. In particular, it is preferred that the plugs of different surgical instruments to be used with the surgical equipment socket, preferably in a surgical system as described herein, are adapted differently, such that plugs of different kinds of surgical instruments contact the plug contact portions of different indicator assemblies.

Further, it is preferred that the first return element is formed as a spiral spring and/or a torsion spring. Preferably, the first return element is positioned between the first movable element and the first pivot axis. Further preferably, the second return element is formed as a spiral spring and/or a torsion spring. Further it is preferred that the second return element is positioned between the second movable element and the second pivot axis. These embodiments are particularly preferred in order to provide a reliable and cost-effective solution, which is easy to produce and/or to mount.

According to a further preferred embodiment, the surgical equipment socket comprises at least one contact opening for receiving at least one contact pin of a plug of a surgical instrument. Preferably, the surgical equipment socket comprises two or more contact openings for receiving two or more contact pins of plugs of different surgical instruments.

It is particularly preferred that the first movable element of the first indicator assembly is moveable upon insertion of a first plug of a first surgical instrument into the surgical equipment socket. It is further preferred that the second movable element of the second indicator assembly is moveable upon insertion of a second plug of a second surgical instrument into the surgical equipment socket. It is further preferred that the first movable element of the first indicator assembly and the second movable element of the second indicator assembly are moveable upon insertion of a third plug of a third surgical instrument into the surgical equipment socket.

These particular embodiments are particularly preferred, for example, when a hybrid instrument for high-frequency and ultrasound energy has a first plug, a hybrid instrument for high-frequency and ultrasound energy has a second plug and an ultrasound device has a third plug.

Further advantageous embodiments of the surgical equipment socket, surgical generator, surgical system and method described above can be realized by combining some or all of the preferred features described herein.

According to a further aspect, it is provided a surgical generator comprising a surgical equipment socket as described herein.

According to a further aspect, it is provided a surgical system comprising a surgical generator as described herein and a first surgical instrument having a first plug and a second surgical instrument having a second plug, wherein the first plug of the first surgical instrument is adapted to move the first movable element of the first indicator assembly from the free position to the mated position upon its insertion into the surgical equipment socket.

According to a preferred embodiment of the surgical system, the second plug of the second surgical instrument is adapted not to move the first movable element of the first indicator assembly from the free position to the mated position upon its insertion into the surgical equipment socket, and/or the second plug of the second surgical instrument is adapted to move the second movable element of the second indicator assembly from the free position to the mated position upon its insertion into the surgical equipment socket.

Further preferably, the surgical system comprises a third surgical instrument having a third plug, wherein the third plug of the third surgical instrument is adapted to move the first movable element of the first indicator assembly and the second movable element of the second indicator assembly upon its insertion into the surgical equipment socket.

Further preferably, the surgical system may comprise a fourth surgical instrument having a fourth plug, wherein the fourth plug of the fourth surgical instrument is adapted to move neither the first movable element of the first indicator assembly nor the second movable element of the second indicator assembly upon its insertion into the surgical equipment socket.

According to a preferred embodiment of the surgical system, the surgical system comprises a control unit adapted to generate a signal depending on whether the first detection element has detected that the first movable element is in the mated position and/or whether the second detection element has detected that the second movable element is in the mated position.

Preferably, the signal is indicative of whether the first, second or third surgical instrument is inserted into the surgical equipment socket.

According to a further aspect, it is provided a method for detecting the use of a surgical instrument in a surgical system, the surgical system comprising surgical generator and a first surgical instrument having a first plug and a second surgical instrument having a second plug, the method comprising inserting the first plug of the first surgical instrument into the surgical equipment socket and detecting whether a first movable element of a first indicator assembly is in a mated position.

According to a preferred embodiment, the method comprises removing the first plug of the first surgical instrument from the surgical equipment socket, and/or inserting the second plug of the second surgical instrument into the surgical equipment socket and detecting whether the first movable element of the first indicator assembly is in the mated position, and/or whether a second movable element of a second indicator assembly is in a mated position, and/or removing the second plug of the second surgical instrument from the surgical equipment socket, and/or inserting a third plug of a third surgical instrument into the surgical equipment socket and detecting whether the first movable element of the first indicator assembly is in the mated position and whether the second movable element of the second indicator assembly is in the mated position, and/or removing the third plug of the third surgical instrument from the surgical equipment socket.

As to the advantages, preferred embodiments and details of the individual different aspects and their preferred embodiments, reference is also made to the corresponding advantages, preferred embodiments and details described with reference to the respective other aspects.

Further advantageous embodiments result from the combination of individual, several or all of the preferred features described herein.

Figure 2:
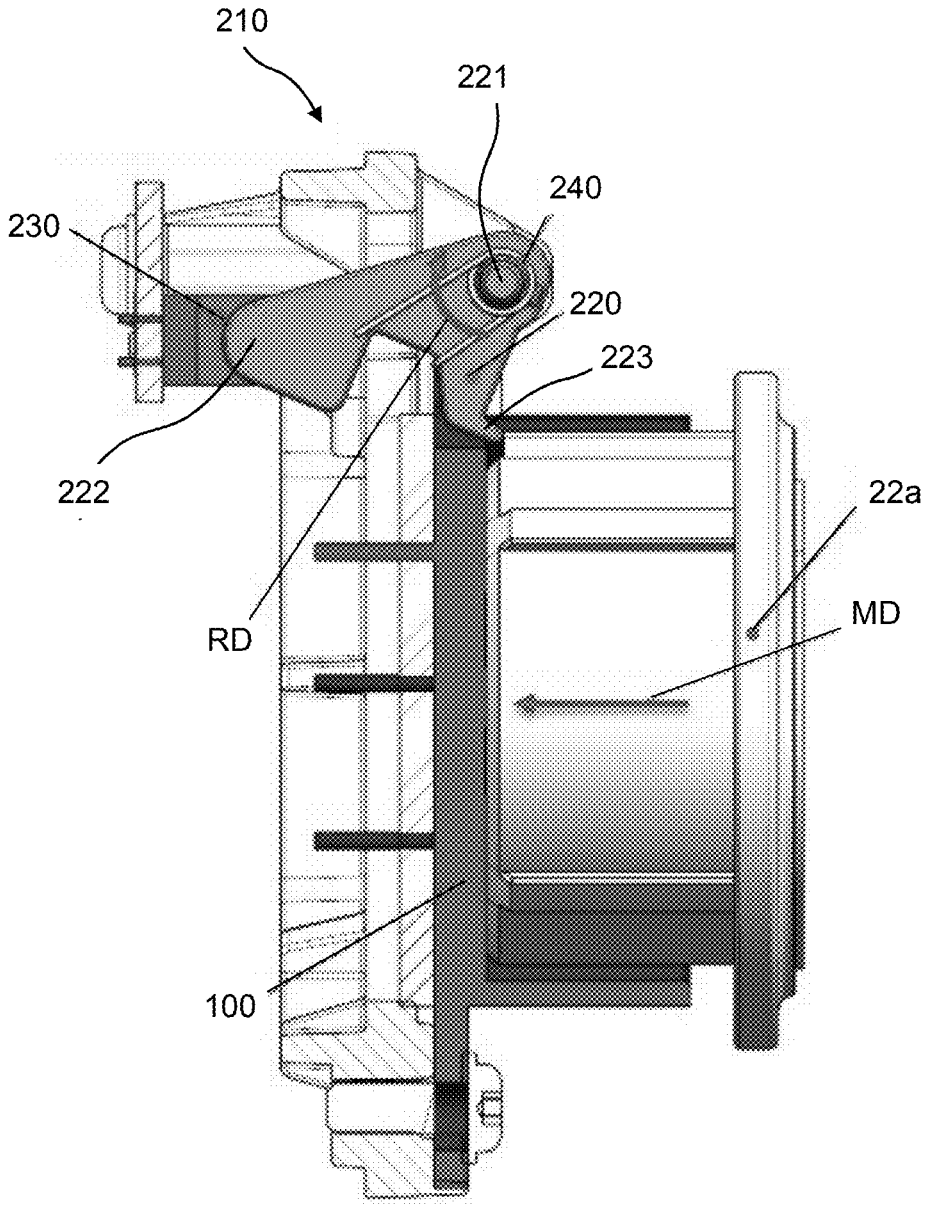
Figure 3:
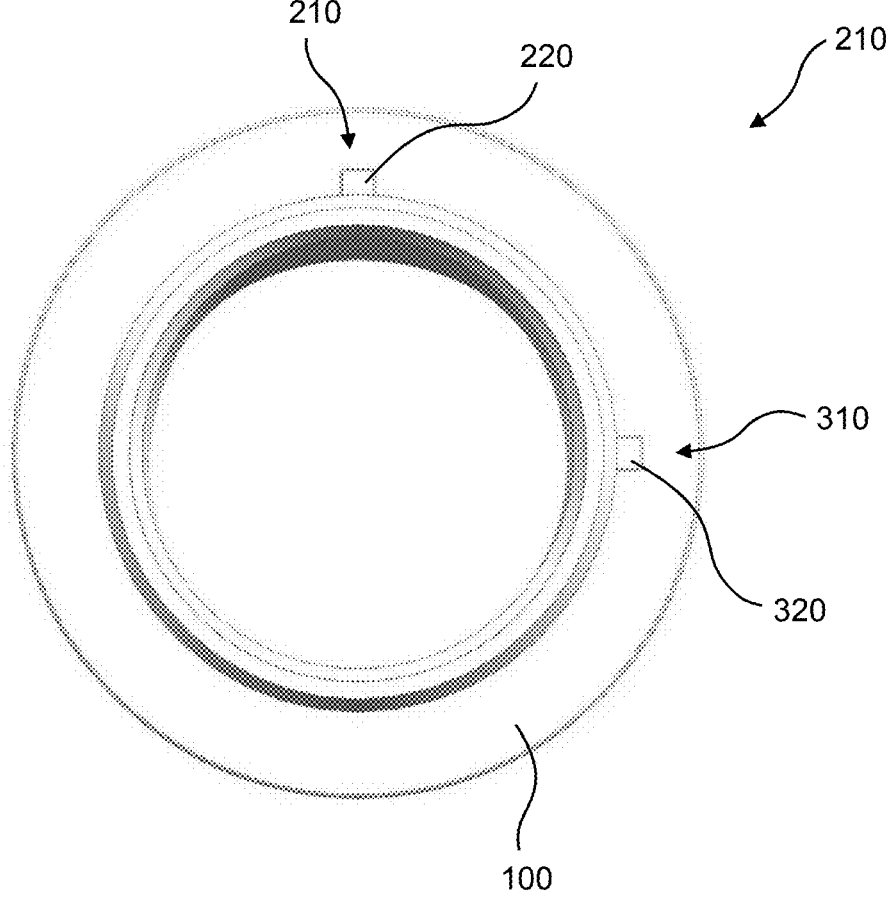
Figure 4:
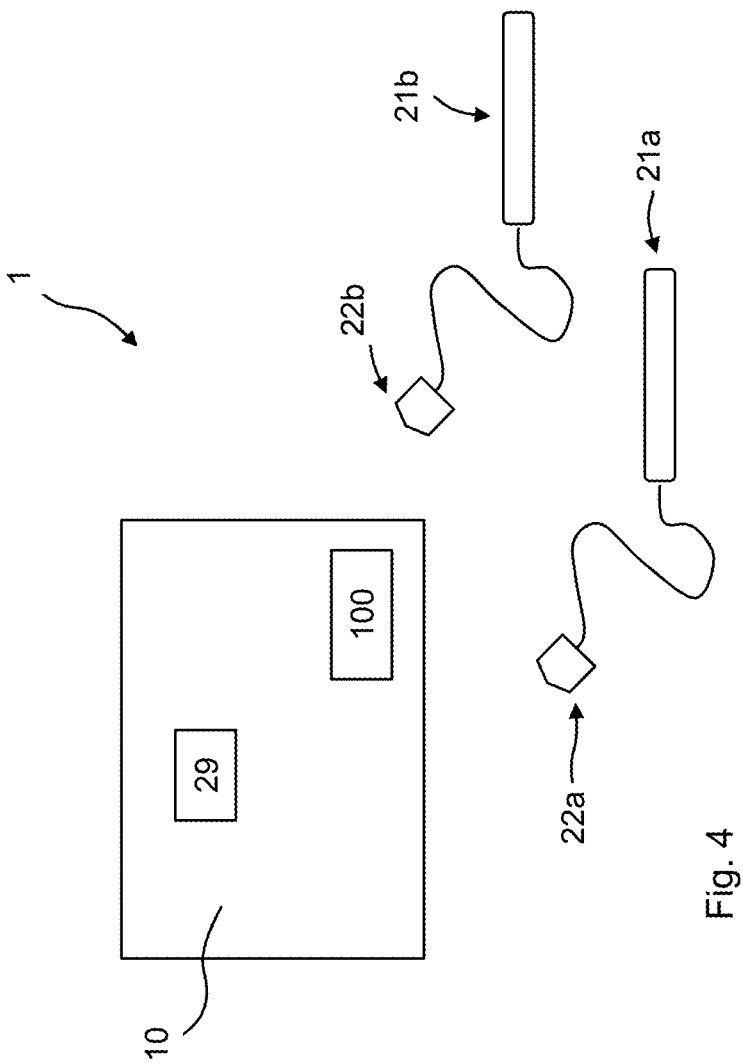
Figure 5:
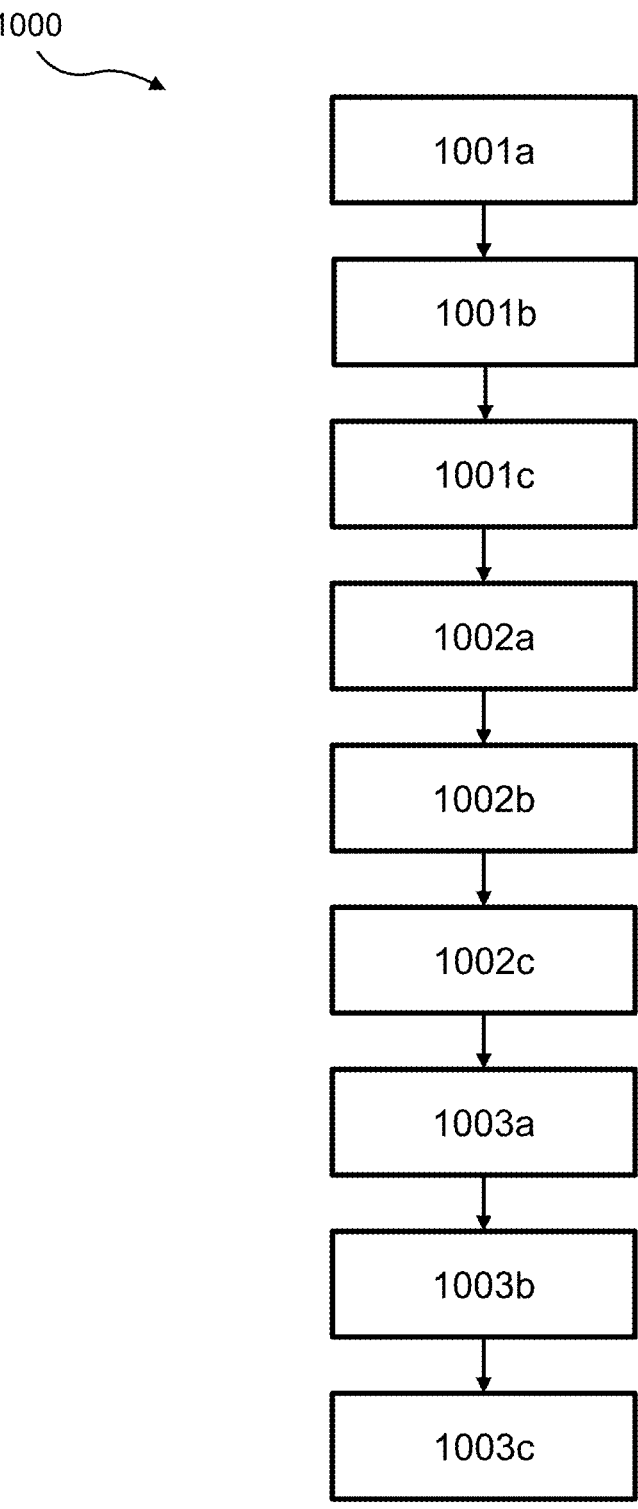

Preferred embodiments shall now be described with reference to the attached drawings, in which FIG. 1: shows a longitudinal section of an exemplary surgical equipment socket in the free position;

FIG. 2: shows a longitudinal section of the surgical equipment socket in the mated position;

FIG. 3: shows a section of the surgical equipment socket;

FIG. 4: shows a schematic representation of an exemplary surgical system;

FIG. 5: shows a schematic representation of an exemplary method for detecting the use of a surgical instrument in a surgical system;

In the figures, elements with the same or comparable functions are indicated with the same reference numerals.

In the longitudinal section of an exemplary surgical equipment socket 100 of FIG. 1, the surgical equipment socket 100 is shown a position, where the first plug 22a is not yet inserted into the surgical open socket 100. FIG. 2 shows the surgical equipment socket 100 of FIG. 1 in a position where the first plug 22a has been inserted into the surgical equipment socket 100. The first plug 22a is inserted into the surgical equipment socket 100 in a mating direction MD. As can be seen from a comparison of FIGS. 1 and 2, the first plug 22a of a first surgical instrument in FIG. 1 is not yet inserted into the surgical equipment socket 100, but is inserted into the surgical equipment socket 100 in FIG. 2. This insertion of the first plug 22a of a first surgical instrument corresponds to a movement of the first plug 22a of the first surgical instrument along the mating direction MD.

The surgical equipment socket 100 has a first indicator assembly 210. As can be seen from FIG. 3, the surgical equipment socket 100 preferably has a second indicator assembly 310. As can be seen from FIG. 3, the first indicator assembly 210 in the second indicator assembly 310 are spaced apart circumferentially.

Preferably, the second indicator assembly 310 is designed in a similar or identical manner as the first indicator assembly 210. Therefore, the detailed description of the first indicator assembly 210 with respect to FIGS. 1 and 2 likewise applies to the details of the second indicator assembly 310, unless stated otherwise.

The first indicator assembly 210 comprises a first movable element 220, which is movable from a free position shown in FIG. 1 to a mated position shown in FIG. 2. The first movable element 220 is movable in a rotational movement direction RD from the free position to the mated position and vice versa. The first movable element 220 is rotatably supported about a first pivot axis 221. The first indicator assembly 210 further comprises a first return element 240, adapted to move the first movable element 220 from the mated position to the free position. The first return element 240 is formed as a spiral spring and positioned between the first movable element 220 and the first pivot axis 221. The first movable element 220 is biased in the free position by the first return element 240.

Further, the first movable element 220 has a first detection portion 222 and a first plug contact portion 223. Further, the surgical department socket 100 comprises a first detection element 230, which comprises a switch, for example, in the form of a light barrier. As described above, other types of switches and other types of detection elements can be employed. The first indicator assembly 210 is adapted such that the first detection portion 222, when the first movable element 220 is in the mating position as shown in FIG. 2, activates the switch of the first detection element 230, such that the first detection element 230 detects that the first movable element 220 is in the mated position.

Preferably, the surgical equipment socket 100 is used in a surgical system 1 as shown in FIG. 4 as an example. The surgical system 1 has a surgical generator 10 having a surgical equipment socket 100. Further, the surgical system 1 comprises a first surgical instrument 21a having a first plug 22a and a second surgical instrument 21b having a second plug 22b. Preferably, the surgical system 1 may have a third surgical instrument (not shown) having a third plug (not shown). Further preferably, the surgical system 1 comprises a control unit 29.

For example, the first surgical instrument 21a may be a first hybrid instrument for high-frequency and ultrasound energy, the second surgical instrument 21b may be a second hybrid instrument for high-frequency and ultrasound energy and the third surgical instrument may be an ultrasound device.

Preferably, the first plug 22a of the first surgical instrument 21a is adapted to move the first movable element 220 of the first indicator assembly 210 in a rotational movement direction RD about the first pivot axis 221 from the free position into the mated position upon its insertion into the surgical equipment socket 100. Preferably, this is effected by the first plug 22a contacting the first plug contact portion 223 of the first movable element 220. By this rotational movement of the first movable element 220, its first detection portion 222 activates the first detection element 230 such that it detects that the first movable element 220 is in the mated position and the control unit 29 generates a corresponding signal. When the first plug 22a of the first surgical instrument 21a is removed from the surgical equipment socket 100, the first return element 240 moves the first movable element 220 from the mated position back to the free position.

The second plug 22b of the second surgical instrument 21b is adapted to move the second movable element 320 of the second indicator assembly 310 from the free position into the mated position upon its insertion into the surgical equipment socket 100. Further preferably, a third plug of a third surgical instrument is adapted to move the first movable element 220 of the first indicator assembly 210 and the second movable element 320 of the second indicator assembly 310 from the mated into the free position upon its insertion into the surgical equipment socket 100.

The control unit 29 is adapted to generate signals according to whether the first detection element 230, the second detection element or both, or none of them is in the mated position. In this way, different plugs belonging to different surgical instruments can be detected.

FIG. 5 schematically depicts a method 1000 for detecting the use of a surgical instrument in a surgical system 1. In a step 1001a, the first plug 22a of the first surgical instrument 21a is inserted into the surgical equipment socket 100 and in a further step 1001b it is detected whether a first movable element 220 of a first indicator assembly 210 is in a mated position.

Further, in step 1001c the first plug 22a of the first surgical instrument 21a is removed from the surgical equipment socket 100, before in a step 1002a the second plug 22b of the second surgical instrument 21b is inserted into the surgical equipment socket 100 and in step 1002b it is detected whether the first movable element 220 of the first indicator assembly 210 is in the mated position, and/or whether the second movable element 320 of the second indicator assembly 310 is in the mated position. Preferably, in step 1002c the second plug 22b of the second surgical instrument 21b is removed from the surgical equipment socket 100. In step 1003a a third plug of a third surgical instrument is inserted into the surgical equipment socket 100 and in step 1003b it is detected whether the first movable element 220 of the first indicator assembly 210 is in the mated position and whether the second movable element 320 of the second indicator assembly 310 is in the mated position.

Further preferably, in step 1032c the third plug of the third surgical instrument from the surgical equipment socket 100 is removed.

The steps as described herein can be performed in the order described, but also can be performed in any other feasible order. In particular, the different plugs can be inserted and preferably removed in any order.

REFERENCE SIGNS 1 surgical system
10 surgical generator
21a first surgical instrument
21b second surgical instrument
22a first plug
22b second plug
100 surgical equipment socket
210 first indicator assembly
220 first movable element
230 first detection element
240 first return element
221 first pivot axis
222 first detection portion
223 first plug contact portion
310 second indicator assembly
320 second movable element
RD rotational movement direction
MD mating movement direction
1000 method for detecting the use of a surgical instrument in a surgical system
1001a inserting the first plug of the first surgical instrument into the surgical equipment socket
1001b detecting whether a first movable element of a first indicator assembly is in a mated position
1001c removing the first plug of the first surgical instrument from the surgical equipment socket
1002a inserting the second plug of the second surgical instrument into the surgical equipment socket
1102b detecting whether the first movable element of the first indicator assembly is in the mated position and/or whether a second movable element of a second indicator assembly is in a mated position
1001c removing the second plug of the second surgical instrument from the surgical equipment socket
1003a inserting a third plug of a third surgical instrument into the surgical equipment socket 1003*b* detecting whether the first movable element of the first indicator assembly is in the mated position and whether the second movable element of the second indicator assembly is in the mated position 1003*c* removing the third plug of the third surgical instrument from the surgical equipment socket

The invention claimed is:

1. A surgical equipment socket for a surgical generator for connecting surgical instruments, the surgical equipment socket comprising:

a first indicator assembly having a first movable element, and a first detection element; and a first plug that is disposed within the surgical equipment socket and disposed parallel to a first plug contact position of the first movable element, the first plug contact position is disposed within the surgical equipment socket;

wherein the first movable element is movable from a free position to a mated position, and wherein the first detection element is adapted to detect whether the first movable element is in the mated position.

2. The surgical equipment socket according to claim 1, comprising:

a second indicator assembly having a second movable element, and a second detection element; wherein the second movable element is movable from a free position to a mated position, and wherein the second detection element is adapted to detect whether the second movable element is in the mated position.

3. The surgical equipment socket according to claim 1, wherein the first movable element is movable in a rotational movement direction from the free position to the mated position, and/or the first movable element is rotatably supported about a first pivot axis, and/or wherein a second movable element is movable in a rotational movement direction from the free position to the mated position, and/or the second movable element is rotatably supported about a second pivot axis.

4. The surgical equipment socket according to claim 1, wherein the first indicator assembly comprises a first return element, wherein the first return element is adapted to move the first movable element from the mated position to the free position, and/or wherein a second indicator assembly comprises a second return element, wherein the second return element is adapted to move a second movable element from the mated position to the free position.

5. The surgical equipment socket according to claim 4, wherein the first detection element comprises a switch, and/or a sensor, and/or wherein a second detection element comprises a switch, and/or a sensor.

6. The surgical equipment socket according to claim 4, wherein the first return element is formed as a spiral spring and/or a torsion spring, and/or wherein the first return element is positioned between the first movable element and a first pivot axis, and/or wherein the second return element is formed as a spiral spring and/or a torsion spring, and/or wherein the second return element is positioned between the second movable element and a second pivot axis.

7. The surgical equipment socket according to claim 1, wherein the first indicator assembly and a second indicator assembly are spaced apart circumferentially, and/or wherein the first movable element has a first detection portion and/or a first plug contact portion, and/or wherein a second movable element has a second detection portion and/or a second plug contact portion.

8. The surgical equipment socket according to claim 1, comprising: at least one contact opening for receiving at least one contact pin of a plug of a surgical instrument.

9. The surgical equipment socket according to claim 1, wherein the first movable element of the first indicator assembly is moveable upon the first plug of a first surgical instrument moving along a mating direction into the surgical equipment socket, and/or wherein a second movable element of a second indicator assembly is moveable upon a second plug of a second surgical instrument moving along a mating direction into the surgical equipment socket, and/or wherein the first movable element of the first indicator assembly and the second movable element of the second indicator assembly are moveable upon a third plug of a third surgical instrument moving along a mating direction into the surgical equipment socket.

10. A surgical generator, comprising:

a surgical equipment socket according to claim 1.

11. A surgical system, comprising:

a surgical generator according to claim 10, and a first surgical instrument having a first plug and a second surgical instrument having a second plug, wherein the first plug of the first surgical instrument is adapted to move the first movable element of the first indicator assembly from the free position to the mated position upon its insertion into the surgical equipment socket.

12. The surgical system according to claim 11, wherein the second plug of the second surgical instrument is adapted not to move the first movable element of the first indicator assembly from the free position to the mated position upon its insertion into the surgical equipment socket, and/or wherein the second plug of the second surgical instrument is adapted to move a second movable element of a second indicator assembly from the free position to the mated position upon its insertion into the surgical equipment socket.

13. The surgical system according to claim 12, comprising:

a third surgical instrument having a third plug, wherein the third plug of the third surgical instrument is adapted to move the first movable element of the first indicator assembly and a second movable element of a second indicator assembly upon its insertion into the surgical equipment socket, and/or a control unit adapted to generate a signal depending on whether the first detection element has detected that the first movable element is in the mated position and/or whether a second detection element has detected that the second movable element is in the mated position.

14. The surgical equipment socket according to claim 1, wherein the first plug moves in a mating direction and towards the first movable element causing the first movable element to move into the mated position.

15. A method for detecting a use of a surgical instrument in a surgical system, the surgical system comprising:

a surgical generator including a surgical equipment socket;

a first surgical instrument having a first plug; and a second surgical instrument having a second plug, the method comprising:

inserting the first plug of the first surgical instrument into the surgical equipment socket and detecting whether a first movable element of a first indicator assembly is in a mated position, such that, when inserted, the first plug is disposed within the surgical equipment socket and disposed parallel to a first plug contact position of the first movable element, and the first plug contact position is disposed within the surgical equipment socket.

16. The method according to claim 15, further comprising:

removing the first plug of the first surgical instrument from the surgical equipment socket, and/or inserting the second plug of the second surgical instrument into the surgical equipment socket and detecting whether the first movable element of the first indicator assembly is in the mated position, and/or whether a second movable element of a second indicator assembly is in a mated position, and/or removing the second plug of the second surgical instrument from the surgical equipment socket, and/or inserting a third plug of a third surgical instrument into the surgical equipment socket and detecting whether the first movable element of the first indicator assembly is in the mated position and whether the second movable element of the second indicator assembly is in the mated position, and/or removing the third plug of the third surgical instrument from the surgical equipment socket.

\* \* \* \* \*